(12) United States Patent
Goronzy et al.

(10) Patent No.: US 6,635,433 B1
(45) Date of Patent: Oct. 21, 2003

(54) METHODS AND MATERIALS FOR DIAGNOSING UNSTABLE ANGINA

(75) Inventors: Jorg J. Goronzy, Rochester, MN (US); Cornelia M. Weyand, Rochester, MN (US); Giovanna Liuzzo, Rome (IT)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/700,677

(22) Filed: Mar. 6, 2001

Related U.S. Application Data

(60) Provisional application No. 60/098,120, filed on Aug. 27, 1998.

(51) Int. Cl.⁷ .............................................. G01N 33/53
(52) U.S. Cl. ......................................................... 435/7.24
(58) Field of Search ......................................... 435/7.24

(56) References Cited

U.S. PATENT DOCUMENTS

| | | | |
|---|---|---|---|
| 5,424,187 A | 6/1995 | Shor et al. .................... 435/6 |
| 5,830,874 A | 11/1998 | Shor et al. .................... 514/29 |
| 5,849,578 A | 12/1998 | Falb ........................... 435/325 |
| 6,040,147 A | * 3/2000 | Ridker et al. .............. 435/7.24 |

OTHER PUBLICATIONS

Liuzzo et al, Circulation, 101, 2883–2888, 2000.*
Liuzzo et al., "Coronary artery disease and inflammation: reflection of underlying disease or repetitive ischemia," *Fibrinolysis & Proteolysis*, 1997, 11(Suppl. 1):155–157.
Liuzzo et al., "Disease Specific Patterns of Cytokine Production by T–Lymphocytes in Coronary Atherosclerosis: Evidence for a Role of Infectious Agents in Pathogenesis of Unstable Agnina?" *J. Am. College Cardiol.*, 1998, (31(2–Suppl. A):187A.
Simon et al., "Makers of T–Lymphocyte Activation are Elevated in Stable Angina but not Unstable Angina," *Circulation*, 1996, 94(8):I81.
Blumgart et al., *Am. Heart Journal*, 1940, 19(1):1–91.
Boise et al., *Immunity*, 1995, 3:87–98.
Fuster et al., *N. Engl. J. Med.*, 1992, 326(5):310–318.
Jung et al., *J. Immunol. Methods*, 1993, 159:197–207.
Linsley et al., *Annu. Rev. Immunol.*, 1993, 11:191–212.
Prussin et al., *J. Immunol. Methods*, 1995, 188:117–128.
Schmidt et al., *Molec. Med.*, 1996, 2(5):608–618.
Vallejo et al., *J. Biol. Chem.*, 1998, 273(14):8119–8129.

* cited by examiner

*Primary Examiner*—David Saunders
(74) *Attorney, Agent, or Firm*—Fish & Richardson P.C., P.A.

(57) ABSTRACT

The invention provides methods and materials for diagnosing an angina condition in a patient. Specifically, the invention provides methods and materials for classifying an angina condition as either stable or unstable. In addition, the invention provides methods and materials for determining an individual's predisposition to have a stable or unstable angina condition. The invention also provides kits for classifying an angina condition as either stable or unstable as well as kits for determining an individual's predisposition to have a stable or unstable angina condition.

10 Claims, 8 Drawing Sheets

METHODS AND MATERIALS FOR DIAGNOSING UNSTABLE ANGINA

This application is the National Stage of International Application No. PCT/US99/19536, filed Aug. 27, 1999, which claims benefit of U.S. Provisional Application No. 60/098,120, filed Aug. 27, 1998.

BACKGROUND

1. Technical Field

The invention relates to methods and materials for diagnosing unstable angina as well as for determining an individual's predisposition to have an unstable angina condition.

2. Background Information

Coronary artery disease is characterized by long periods of clinical stability with few or no symptoms. In addition, classical pathologic studies have demonstrated that the disease is commonly far advanced anatomically before any symptoms are reported (Blumgart HL et al., *Am. Heart Journal*, 19:1 (1940)). An additional characteristic of coronary artery disease is a propensity to an abrupt, sometimes catastrophic, change in a previous stable or silent clinical course leading to a variety of acute coronary syndromes (Fuster V et al., *N. Engl. J. Med.* 326:310–318 (1992)). The fundamental mechanism responsible for provoking such abrupt changes in clinical status of patients with coronary artery disease is unresolved.

SUMMARY

The invention involves methods and materials for diagnosing an unstable angina condition in a patient. Specifically, the invention provides methods and materials for classifying an angina condition as either stable or unstable. In addition, the invention provides methods and materials for determining an individual's predisposition to have a stable or unstable angina condition.

The invention is based on the discovery that the frequency of cytokine-producing cells within a patient suffering from an angina condition can be used to help a clinician determine whether that condition is stable or unstable. Specifically, the invention involves determining the frequency of cytokine-producing cells in a patient and determining whether that frequency corresponds to the frequencies found in 1) healthy individuals, 2) stable angina patients, or 3) unstable angina patients. For example, unstable angina patients tend to have an elevated frequency of both $CD4^+$ and $CD8^+$ T cells that produce INF-γ.

The invention also is based on the discovery that the frequency of $CD4^+/CD28^{null}$ cells within a patient suffering from an angina condition can be used to help a clinician determine whether that condition is stable or unstable. Specifically, the invention involves determining the frequency of $CD4^+/CD28^{null}$ cells in a patient and determining whether that frequency corresponds to the frequencies found in 1) healthy individuals, 2) stable angina patients, or 3) unstable angina patients. For example, unstable angina patients tend to have an elevated frequency of $CD4^+/CD28^{null}$ cells.

Determining whether an angina condition is stable or unstable is important for determining the proper course of treatment. Briefly, an unstable angina condition is much more serious than a stable angina condition and requires much more intense clinical attention. Thus, if clinicians can determine the stable or unstable nature of angina condition, patient's suffering from an angina condition can be diagnosed and treated appropriately.

In addition, the invention is based on the discovery that the frequency of cytokine-producing cells as well as the frequency of $CD4^+/CD28^{null}$ cells in a individual can be used to determine the individual's predisposition to have a stable or unstable angina condition. Specifically, the invention involves determining the frequency of cytokine-producing cells and/or the frequency of $CD4^+/CD28^{null}$ cells in an individual and determining whether those frequencies correspond to the frequencies found in stable angina patients or unstable angina patients.

Determining whether an individual is predisposed to have a stable or unstable angina condition can help individuals prepare for and prophylactically treat potentially life-threatening disease. For example, once individuals learn of their predisposition they can change their diet and daily activities such that the chance of developing an unstable angina condition is reduced.

In general, the invention features a method for diagnosing an angina condition in a patient. This method involves stimulating lymphocytes (e.g., $CD4^+$ or $CD8^+$ cells) from the patient, determining the frequency of cytokine-producing cells among the lymphocytes, comparing the frequency of cytokine-producing cells to a reference frequency to obtain information about the patient's angina condition, and classifying the angina condition as stable or unstable based on the information. A phorbol ester (e.g., phorbol myristate acetate) or a calcium ionophore (e.g., ionomycin) can be used to stimulate the lymphocytes. The frequency of cytokine-producing cells can be the percent of $CD4^+$ cells producing INF-γ, the percent of $CD8^+$ cells producing INF-γ, the percent of $CD4^+$ cells producing IL-2, or the percent of $CD4^+$ cells producing IL-4. The reference frequency can be the median frequency of cytokine-producing cells derived from a population (e.g., a population of unstable angina patients, stable angina patients, or healthy individuals). For example, the median frequency of cytokine-producing cells can be the median percent of $CD4^+$ cells producing INF-γ derived from a population, the median percent of $CD8^+$ cells producing INF-γ derived from a population, the median percent of $CD4^+$ cells producing IL-2 derived from a population, or the median percent of $CD4^+$ cells producing IL-4 derived from a population.

In another embodiment, the invention features a method for determining the predisposition of an individual to have a stable or unstable angina condition. This method involves stimulating lymphocytes from the individual, determining the frequency of cytokine-producing cells among the lymphocytes, comparing the frequency of cytokine-producing cells to a reference frequency to obtain information about the individual, and classifying the individual as being predisposed to have a stable or unstable angina condition based on the information.

The invention also features a method for diagnosing an angina condition in a patient. This method comprises determining the frequency of $CD4^+/CD28^{null}$ cells in the patient, comparing the frequency of $CD4^+/CD28^{null}$ cells to a reference frequency to obtain information about the angina condition, and classifying the angina condition as stable or unstable based on the information. The frequency of $CD4^+/CD28^{null}$ cells can be the percent of $CD4^+$ cells that are CD28 negative. The reference frequency can be derived from the $CD4^+/CD28^{null}$ cell frequencies from a population (e.g., a population of unstable angina patients, stable angina patients, or healthy individuals). In addition, the reference frequency can be the percent of $CD4^+$ cells that are CD28 negative. For example, the reference frequency can be greater than about 2.0 percent or less than about 2.0 percent.

In another embodiment, the invention features a method for determining the predisposition of an individual to have a stable or unstable angina condition. This method involves determining the frequency of $CD4^+/CD28^{null}$ cells in the individual, comparing the frequency of $CD4^+/CD28^{null}$ cells to a reference frequency to obtain information about the individual, and classifying the individual as being predisposed to have a stable or unstable angina condition based on the information.

In another aspect, the invention features a kit for providing diagnostic information about an angina condition in a patient. The kit contains a binding pair member and a reference chart. The binding pair member has a specific binding affinity for a cytokine such that the frequency of cells producing the cytokine from the patient is determinable. The reference chart contains information about cytokine-producing cell frequencies such that an indication of the stable or unstable nature of the angina condition is determinable based on the frequency of cells producing the cytokine from the patient.

In another embodiment, the invention features a kit for determining the predisposition of an individual to have a stable or unstable angina condition. The kit contains a binding pair member and a reference chart. The binding pair member has a specific binding affinity for a cytokine such that the frequency of cells producing the cytokine from the individual is determinable. The reference chart contains information about cytokine-producing cell frequencies such that an indication of the predisposition is determinable based on the frequency of cells producing the cytokine from the individual.

The invention also features a kit for providing diagnostic information about an angina condition in a patient. The kit contains a binding pair member and a reference chart. The binding pair member has a specific binding affinity for a $CD4^+/CD28^{null}$ cell marker such that the frequency of $CD4^+/CD28^{null}$ cells in the patient is determinable. The reference chart contains information about $CD4^+/CD28^{null}$ cell frequencies such that an indication of the stable or unstable nature of the angina condition is determinable based on the frequency of $CD4^+/CD28^{null}$ cells in the patient.

In another embodiment, the invention features a kit for determining the predisposition of an individual to have a stable or unstable angina condition. The kit contains a binding pair member and a reference chart. The binding pair member has a specific binding affinity for a $CD4^+/CD28^{null}$ cell marker such that the frequency of $CD4^+/CD28^{null}$ cells in the individual is determinable. The reference chart contains information about $CD4^+/CD28^{null}$ cell frequencies such that an indication of the predisposition is determinable based on the frequency of $CD4^+/CD28^{null}$ cells in the individual.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1A:
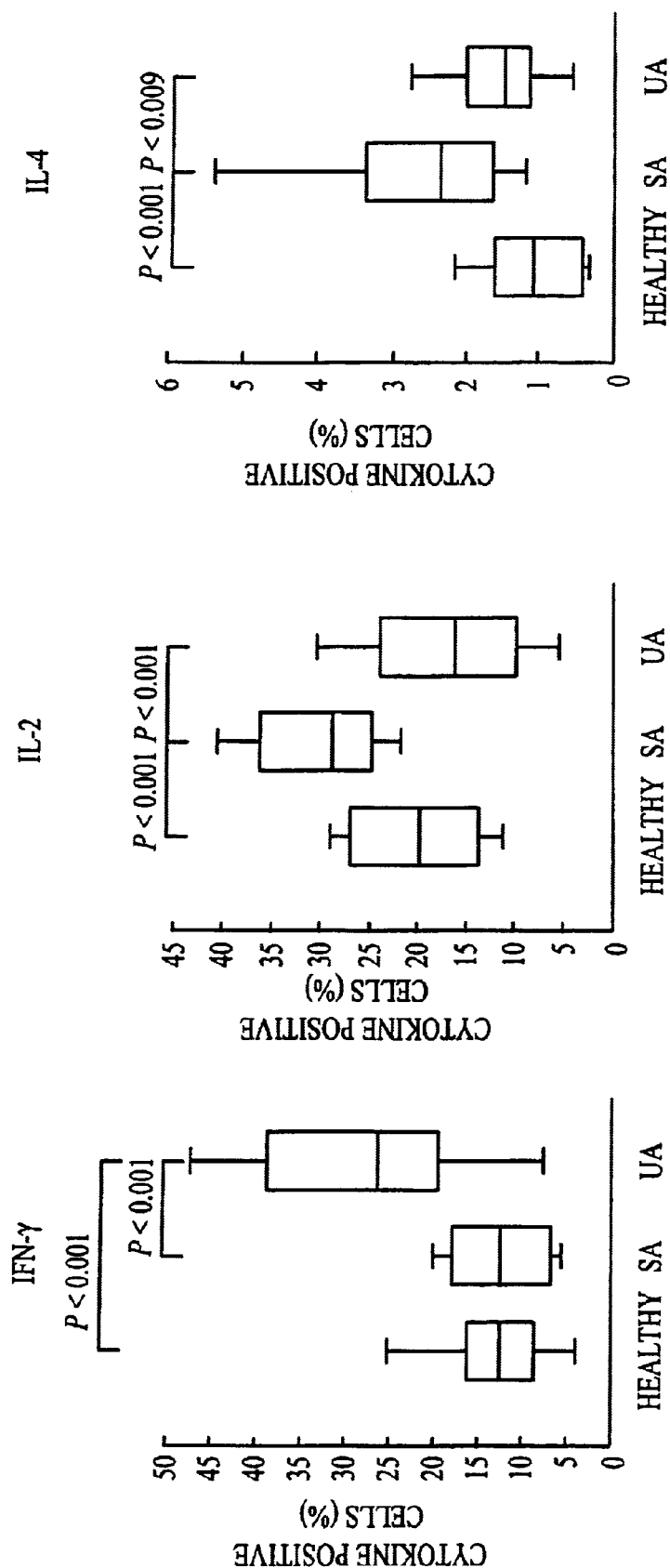
FIG. 1 is a series of graphs plotting the percent of IFN-γ, IL-2, or IL-4 positive cells from healthy individuals, stable angina (SA) patients, or unstable angina (UA) patients. Panel A contains the frequencies of $CD4^+$ T lymphocytes producing IFN-γ, IL-2, and IL-4 after in vitro activation, and panel B contains the frequencies of $CD8^+$ T lymphocytes producing IFN-γ, IL-2, and IL-4 after in vitro activation. Data are presented as medians (line within the box), $25^{th}$ and $75^{th}$ percentiles (box), and $10^{th}$ and $90^{th}$ percentiles (whiskers).

The invention provides methods and materials related to the diagnosis of an angina condition in a patient. Specifically, the invention provides methods and materials for classifying an angina condition as either stable or unstable. In addition, the invention provides methods and materials for determining a patient's predisposition to have a stable or unstable angina condition.

The following methods and materials can be used to diagnose an angina condition as stable or unstable. Specifically, cells (e.g., lymphocytes) can be collected from a patient and stimulated. These cells can be $CD4^+$ and/or $CD8^+$ T cells. In addition, any compound or compounds known to stimulate cells can be used. For example, a phorbol ester (e.g., phorbol myristate acetate) and a calcium ionophore (e.g., ionomycin) can be added to the cells. After stimulation, the frequency of cells that produce a cytokine is determined. For example, the percent of $CD4^+$ cells that produce INF-γ, IL-2, or IL-4, or the percent of $CD8^+$ cells that produce INF-γ can be determined. Any method can by used to determine these frequencies including, without limitation, FACS and ELISA spot assay. For example, since cytokines are typically secreted, the cells can be treated such that exocytosis or intracellular trafficking of vesicular compartments is reduced or prevented. Such treatments can include reducing temperature or treatment with Brefeldin A. The cell can then be evaluated for the presence of a particular cytokine using a binding pair member. A binding pair member is any molecule that specifically binds another molecule including, without limitation, antibodies, antibody fragments that have binding specificity, ligands, receptors, lectins, chelating agents, ions, and the like. When determining the frequency of IL-2 producing cells, for example, an antibody that specifically binds IL-2 can be used.

Once a frequency of cytokine-producing cells in a patient is determined, that frequency can be compared to a reference frequency to obtain information about the patient's angina condition. Typically, a reference frequency is derived from the frequencies determined for a population of individuals. For example, a reference frequency can be a median percent of $CD4^+$ cells producing INF-$\gamma$, IL-2, or IL-4, or a median percent of $CD8^+$ cells producing INF-$\gamma$ derived from a population. The population can be a population of unstable angina patients, stable angina patients, or healthy individuals. The information obtained by this comparison can allow the patient's angina condition to be classified as either stable or unstable. For example, if the frequency of IL-2-producing cells from a patient corresponds to the reference frequency of IL-2-producing cells derived from a population of stable angina patients, then that patient's angina condition can be classified as a stable angina condition. Likewise, if the frequency of INF-$\gamma$-producing cells from a patient corresponds to the reference frequency of INF-$\gamma$-producing cells derived from a population of unstable angina patients, then that patient's angina condition can be classified as an unstable angina condition.

Since the frequency of cytokine-producing cells in a particular individual remains stable over time, the methods and materials described herein can be used to determine that individual's predisposition to have a stable or unstable angina condition. For example, if the frequency of INF-$\gamma$-producing cells from an individual corresponds to a reference frequency of INF-$\gamma$-producing cells derived from a population of unstable angina patients, then that individual can be classified as being predisposed to have an unstable angina condition. Again, these reference frequencies are derived from a population (e.g., stable angina patients, unstable angina patients, or healthy individuals).

In another embodiment, the invention involves determining the frequency of $CD4^{+/}CD28^{null}$ cells in a patient to determine whether that patient's angina condition is stable or unstable. Any method can be used to determine the frequency of $CD4^{+/}CD28^{null}$ cells within a patient. For example, a binding pair member having specificity for a marker found on $CD4^{+/}CD28^{null}$ cells can be used to determine the frequency of those cells. Such a method can involve using the combination of two antibodies, one having specificity for CD4 and the other having specificity for CD28. For example, FACS can be used with CD4 and CD28 specific antibodies to determine the percent of $CD4^+$ that are CD28 negative.

Once a frequency of $CD4^{+/}CD28^{null}$ cells in a patient is determined, that frequency can be compared to a reference frequency to obtain information about the patient's angina condition. Typically, a reference frequency is derived from the $CD4^{+/}CD28^{null}$ cell frequencies determined for a population of individuals. For 5 example, a reference frequency can be a median percent of $CD4^+$ cells that are CD28 negative as derived from a population. The population can be a population of unstable angina patients, stable angina patients, or healthy individuals. The information obtained by this comparison can allow the patient's angina condition to be classified as either stable or unstable. For example, if the frequency of $CD4^{+/}CD28^{null}$ cells from a patient corresponds to the reference frequency of $CD4^{+/}CD28^{null}$ cells derived from a population of stable angina patients, then that patient's angina condition can be classified as a stable angina condition. Likewise, if the frequency of $CD4^{+/}CD28^{null}$ cells from a patient corresponds to the reference frequency of $CD4^{+/}CD28^{null}$ cells derived from a population of unstable angina patients, then that patient's angina condition can be classified as an unstable angina condition. Typically, a patient having greater than 2.0 percent of their $CD4^+$ cells being CD28 negative has an unstable angina condition. In addition, a patient having less than 2.0 percent of their $CD4^+$ cells being CD28 negative has a stable angina condition.

Since the frequency of $CD4^{+/}CD28^{null}$ cells in a particular individual remains stable over time, the methods and materials described herein can be used to determine that individual's predisposition to have a stable or unstable angina condition. For example, if the frequency of $CD4^{+/}CD28^{null}$ cells from an individual corresponds to a reference frequency of $CD4^{+/}CD28^{null}$ cells derived from a population of unstable angina patients, then that individual can be classified as being predisposed to have an unstable angina condition. Again, these reference frequencies are derived from a population (e.g., stable angina patients, unstable angina patients, or healthy individuals).

A reference chart is any chart that contains information about any of the reference frequencies described herein. For example, a reference chart can contain information about the average frequency of $CD4^{+/}CD28^{null}$ cells found in stable angina patients, unstable angina patients, and healthy individuals. It will be appreciated that a reference chart can be presented or contained on any type of medium (e.g., paper or electronic formats). It is to be understood that an electronic format can be obtained via a software program or an accessible database site (e.g., an Internet site). For the purpose of this invention, kits containing a reference chart include kits having directions (e.g., access codes or Internet address information) for accessing reference charts in an electronic format.

The invention will be further described in the following examples, which do not limit the scope of the invention described in the claims.

EXAMPLES

Example 1

Functional Profile of Circulating T Lymphocytes Distinguishes Patients With SA and UA 1. Patient Population Twenty-five patients with stable angina (SA) who underwent diagnostic coronary angiography (21 men, 4 women; mean age±SD, 64±10 years) as well as 21 patients admitted to a coronary care unit during the same time interval with a diagnosis of unstable angina, class IIIB of Braunwald's classification (13 men, 8 women; mean age±SD, 68±10 years), were studied. In parallel, 21 healthy individuals of the same age group (11 men, 10 women; mean age±SD, 62±11 years) were studied.

SA patients had no acute events or worsening of symptoms during the previous six months and no anginal episodes within the prior week. UA patients had experienced at least two episodes of angina at rest or one episode lasting more than 20 minutes during the preceding 48 hours; ST segment shift diagnostic for myocardial ischemia during the angina attacks; chest pain in the preceding 24 hours; and no elevation in serum creatine kinase and lactate dehydrogenase on admission and during the first 24 hours of hospitalization. Symptoms of UA started 2–34 days prior to hospital admission. In 12 patients, UA was the first manifestation of coronary artery disease.

Exclusion criteria for both patient groups were: acute myocardial infarction, PTCA, or by-pass surgery within the preceding six months; valvular heart diseases; cardiomyopathies; left ventricular ejection fraction<30%; and left ventricular hypertrophy, left bundle branch block, atrial fibrillation, or other ECG abnormalities. Patients with asthma, allergic diseases, peptic ulcer, hematological and immunological disorders, recent bacterial infections (within the previous three months), fever, connective tissue diseases and other inflammatory diseases, recent surgery or trauma (within the previous three months), known or suspected malignancy, or immunosuppressive therapy were also excluded because of possible confounding effects on immune system activation. Each patient gave informed consent. The clinical characteristics and angiographic findings of SA and UA patients are summarized in Table 1.

TABLE 1

Clinical characteristics and angiographic findings in stable and unstable angina patients.

|  | Stable Angina | Unstable Angina | P |
| --- | --- | --- | --- |
| Number of patients | 25 | 21 | — |
| Age in years, mean and SD | 64 ± 10 | 68 ± 10 | 0.13 |
| Sex (M/F) | 21/4 | 13/8 | 0.11 |
| Risk Factors | 16 (64%) | 15 (71%) | 0.37 |
| Family history of IHD | 13 (52%) | 9 (43%) | 0.75 |
| Hypercholesterolemia | 5 (20%) | 3 (14%) | 0.71 |
| Diabetes | 13 (52%) | 7 (33%) | 0.33 |
| Smoking | 12 (48%) | 10 (48%) | 0.79 |
| Previous history |  |  |  |
| Stable angina | 25 (100%) | 2 (10%) | <0.001 |
| Myocardial infarction (>6 months) | 7 (28%) | 7 (33%) | 0.94 |
| Myocardial revascularization (>6 months) | 9 (36%) | 7 (33%) | 0.90 |
| Unstable angina as first manifestation of CAD | — | 12 (57%) | — |
| Medications |  |  |  |
| Nitrates (oral or topical) | 19 (76%) | 7 (33%) | 0.009 |
| Calcium channel blockers | 6 (24%) | 5 (24%) | 0.74 |
| Beta blockers | 14 (56%) | 14 (67%) | 0.66 |
| Aspirin (81–324 mg/qd) | 23 (92%) | 21 (100%) | 0.49 |
| Ticlopidine | 5 (20%) | 7 (33%) | 0.49 |
| Lipid lowering drugs | 10 (40%) | 9 (43%) | 0.92 |
| Intravenous nitrates | 0 | 13 (62%) | <0.001 |
| Intravenous heparin | 0 | 21 (100%) | <0.001 |
| Angiographic findings |  |  |  |
| Single-vessel disease | 6 (24%) | 8 (31%) | 0.48 |
| Multiple-vessel disease | 17 (68%) | 13 (52%) | 0.48 |
| Intracoronary thrombosis | 4 (16%) | 5 (24%) | 0.71 |
| Complex lesions | 6 (24%) | 8 (28%) | 0.35 |

2. Blood Sampling

Peripheral blood samples were taken immediately after hospitalization, 7–14 days after hospital discharge, and three months after the first sample was collected. In nine SA and eight UA patients, blood samples were obtained simultaneously from the aortic root and the coronary sinus during diagnostic coronary angiography prior to contrast medium injection and drug administration.

3. Cell Preparation

Peripheral blood mononuclear cells (PBMC) were isolated immediately from heparinized blood by density-gradient centrifugation over Ficol-Hypaque (Amersham Pharmnacia Biotech, Arlington Heights, Ill.). Cells were resuspended in RPMI-1640 (Biowhittaker, Walkersville, Md.) supplemented with 10% fetal calf serum (Summit Biotechnologies, Fort Collins, Colo.), 100 U/mL penicillin, 100 $\mu$g/mL streptomycin, and 2 mM L-glutamine (all Life Technologies, Grand Island, N.Y.) at a density of $1 \times 10^7$ cells/mL.

4. Cell Surface Staining

PBMC were stained (20 minutes at 4° C.) with a combination of two of the following monoclonal antibodies, anti-CD3 (fluorescein isothiocyanate [FITC]-conjugated), anti-CD4 (peridinin chlorophyll protein [PerCP]-conjugated), anti-CD8 PerCP-conjugated (all from Becton Dickinson, San Jose, Calif.), and anti-CD28 FITC-conjugated (Pharmigen,. San Diego, CA), and analyzed on a FACS Calibur flow cytometer (Becton Dickinson) to determine the frequencies of $CD3^\circ$ $C.D4^+$, $CD3^+CD8^+$, and $CD4^+CD28^{null}$ T cells. Analysis was performed using WinMIDI software (Joseph Trotter, Scripps Research Institute, La Jolla, Calif.).

5. Flow Cytometric Cytokine Production Assay

Cytokine production by T cell subsets was assessed by three-color flow cytometry (Jung T et al. *J. Immunol. Methods* 159:197–207 (1993) and Pnissin and Metcalfe *J. Immunol. Methods* 188:117–128 (1995)). Briefly, $1 \times 10^7$ PBMC were stimulated in 24-well plates with 10 ng/mL of phorbol myristate acetate (PMA) and 1 $\mu$g/mL Brefeldin A (Epicenter Technologies, Madison, Wis.) was added to the cultures to inhibit cytokine secretion. The cells were incubated for four hours at 37° C. in a humidified incubator in 7.5% $CO_2$. Cell surface staining was performed as described above. The cells were then fixed with 1% paraformaldehyde/PBS for ten minutes, membranes were permeabilized with a PBS solution containing 0.1% saponin and 0.05% sodium azide, and the cells were incubated with PE-labeled anti-cytokine monoclonal antibodies (anti-IFN-$\gamma$, anti-IL-2, and anti-IL-4) or isotype monoclonal antibody controls (all from R&D Systems, Minneapolis, Minn.) for 30 minutes at room temperature, washed two times with PBS/0.1% saponin buffer, fixed again with 1% paraformaldehyde/PBS, and analyzed on a FACS Calibur flow cytometer.

6. Flow Cytometric Analysis

Twenty thousand events were analyzed using WinMDI software. A tight light scatter region was drawn to include only viable lymphocytes. $CD3^+CD4^+$, $CD3^+CD8^+$, $CD4^+CD28^+$, $CD4^+CD28^{null}$ cells were analyzed for their expression of the cytokines of interest. In all experiments, less than 1% of the cells were positive for the isotype controls, demonstrating a veryhigh staining specificity.

7. Statistical Analysis

Comparisons between groups were carried out using the Mann-Whitney test (2 groups) and the Krtiskal Wallis one-way ANOVA (more than 2 groups). Comparisons within groups were carried out using the Friedman test. For a P value<0.05, pairwise comparisons were carried out using the Wilcoxon test with the Bonferroni correction. Correlations were determined using Spearman's rank correlation test. The remaining continuous variables were compared using Student's t-test for paired and unpaired variables, as appropriate. Proportions were compared using the Fisher exact test. P values<0.05 (two-tailed) were considered statistically significant. All statistical analysis was performed using SigmaStat Software (SPSS, Chicago, Ill.).

8. Results

Patients with SA and UA as well as age-matched controls were examined for the capability of circulating T cells to produce the cytokines IFN-$\gamma$, IL-2, and IL-4. In all donors, $CD3^+CD4^+$ and $CD3^+CD8^+$ T cells could be identified that produced these cytokines. The frequencies of IFN-γ, IL-2, and IL-4 producing T cells, however, were different in the two patient cohorts.

Figure 1B:
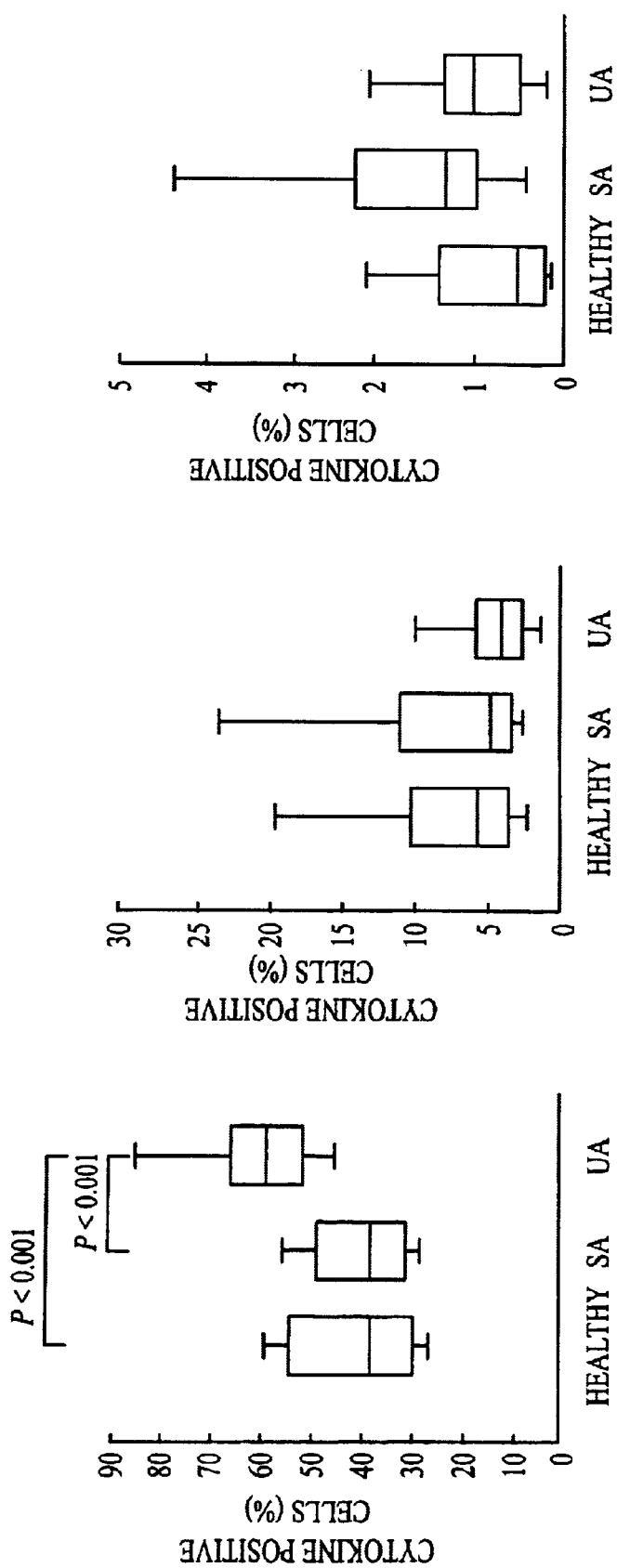

Results of the T cell studies are summarized in FIG. 1. Cells expressing cytoplasmic IFN-γ accounted for 3.6 to 27.2% (median 12.4%) of the peripheral CD4$^+$ T cells in normal donors and for 3.1 to 33.7% (median 12.4%) in patients with SA. In contrast, up to 56% of the T cells in the CD4$^+$ compartment synthesized IFN-γ in patients with UA (median frequency 26.4%, range 7.5 to 56.3%). This feature distinguished UA patients from the healthy controls ($P<0.001$) and the cohort with SA ($P<0.001$). Differences between the two patient subsets in the potential of peripheral CD4$^+$ T cells to produce cytokines were not limited to IFN-γ but also included the production of IL-2 and IL-4. As shown, 5 to 50% of CD4$^+$ T cells synthesized IL-2 polypeptide. Median frequencies of CD4$^+$ IL-2$^+$ T cells were the highest in patients with SA (28.4%i range 17.0 to 48.4%) and were significantly different from those in the control (19.7%, range 10.0 to 31.6%, $P<0.001$) and UA cohorts (16.1%, range 4.9 to 35.3%, $P<0.001$). With respect to IL-2-producing CD4$^+$ T cells, the controls and UA patients were indistinguishable. Also, SA patients had the highest levels of IL-4-containing CD4$^+$ T cells (median, 2.4%, range 1.1 to 7.2%). Production of IL-4 after short-term activation of circulating T cells was identical in control individuals and UA patients.

In summary, the expansion of CD4$^+$ T cells synthesizing IFN-γ was a distinguishing feature for patients with UA. In contrast, patients with SA displayed a distinct cytokine pattern characterized by an increased proportion of CD4$^+$ T cells producing IL-2 and IL-4.

Differences in the functional T cell repertoire also involved CD3$^+$CD8$^+$ T cells. Overall, a marked proportion of circulating CD8$^+$ T cells synthesized IFN-γ. In controls and SA patients, 38.7% (range 21.8 to 63.4%) and 38.5% (range 22.4 to 60.4%), respectively, of CD8$^+$ T cells were positive for IFN-γ. In patients with UA, CD8$^+$IFN-γ$^+$ T cells were extremely frequent, accounting for up to 90% of CD8$^+$ T cells in some of the donors. The median frequency of IFN-γ$^+$CD8$^+$ T cells in UA was 59.2% (range 38.6 to 90.0%) and was significantly increased when compared with controls ($P<0.001$) and SA patients ($P<0.001$). The frequencies of CD8$^+$ cells that synthesized IL-2 were similar in all three study cohorts (2.0 to 25.0%). IL-4 production by CD8$^+$ T cells also did not distinguish the study cohorts (0.1 to 4.8%).

Taken together, patients with UA bore increased frequencies of CD4$^+$ as well as CD8$^+$ T cells with the capability to secrete IFN-γ. This shift in the functional profile was not simply a reflection of heightened T cell activation because it was unique for IFN-γ and did not include IL-2 or IL-4. Rather, increased proportions of CD4$^+$ T cells producing IL-2 and IL-4 were characteristic of patients with SA. These data suggest that angina in its stable and unstable clinical manifestations is associated with two different patterns of perturbation in the functional T cell repertoire.

Example 2

Figure 2:
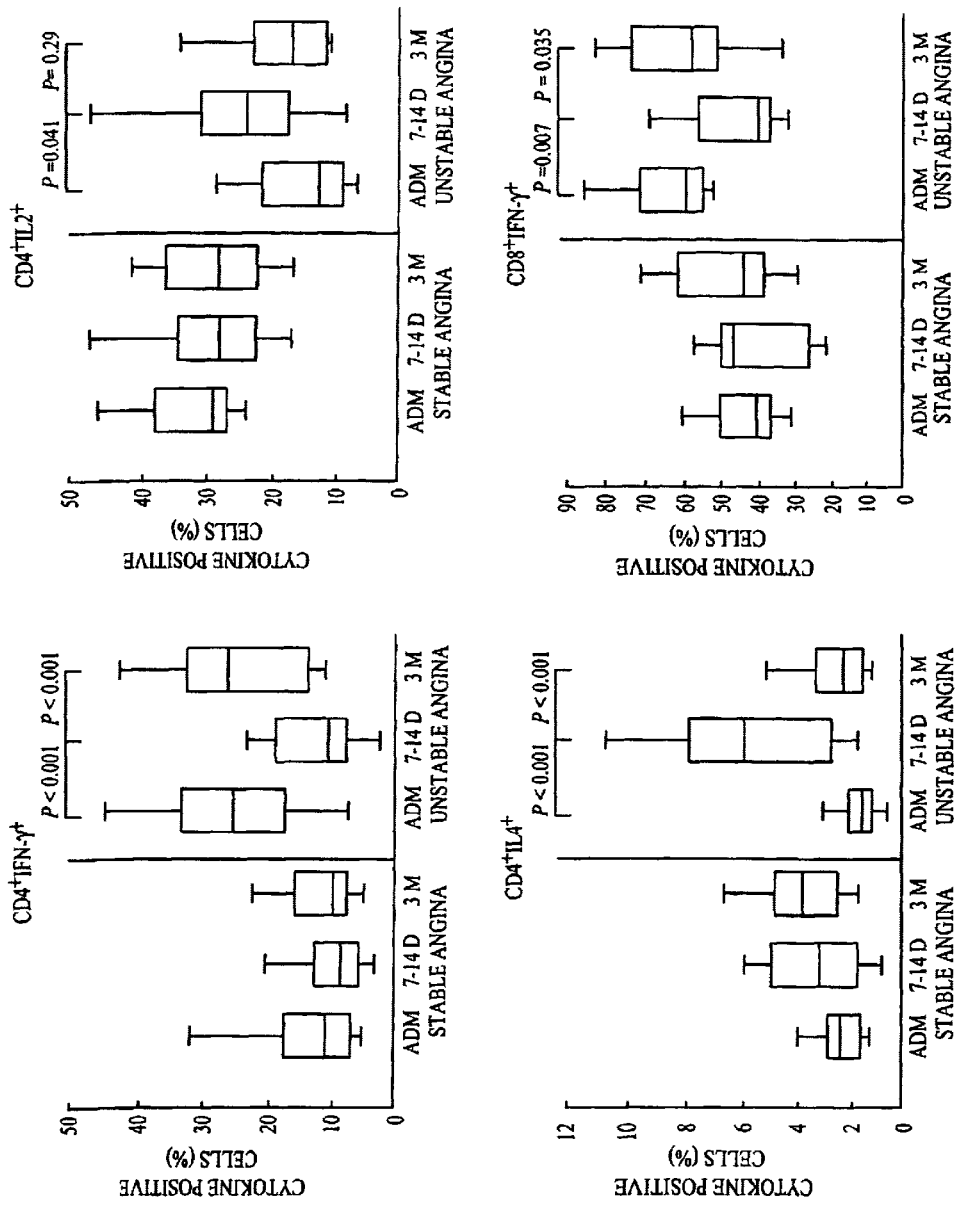
FIG. 2 is a series of graphs plotting the percent of $CD4^+$ T lymphocytes producing IFN-γ, IL-2, and IL-4 as well as the percent of $CD8^+$ T lymphocytes producing IFN-γ for stable and unstable angina patients upon hospital admission (adm), 7–14 days after hospital discharge (7–14 d), and 3 months after admission (3 m). Data are presented as medians (line within the box), $25^{th}$ and $75^{th}$ percentiles (box), and $10^{th}$ and $90^{th}$ percentiles (whiskers).
Figure 3A:
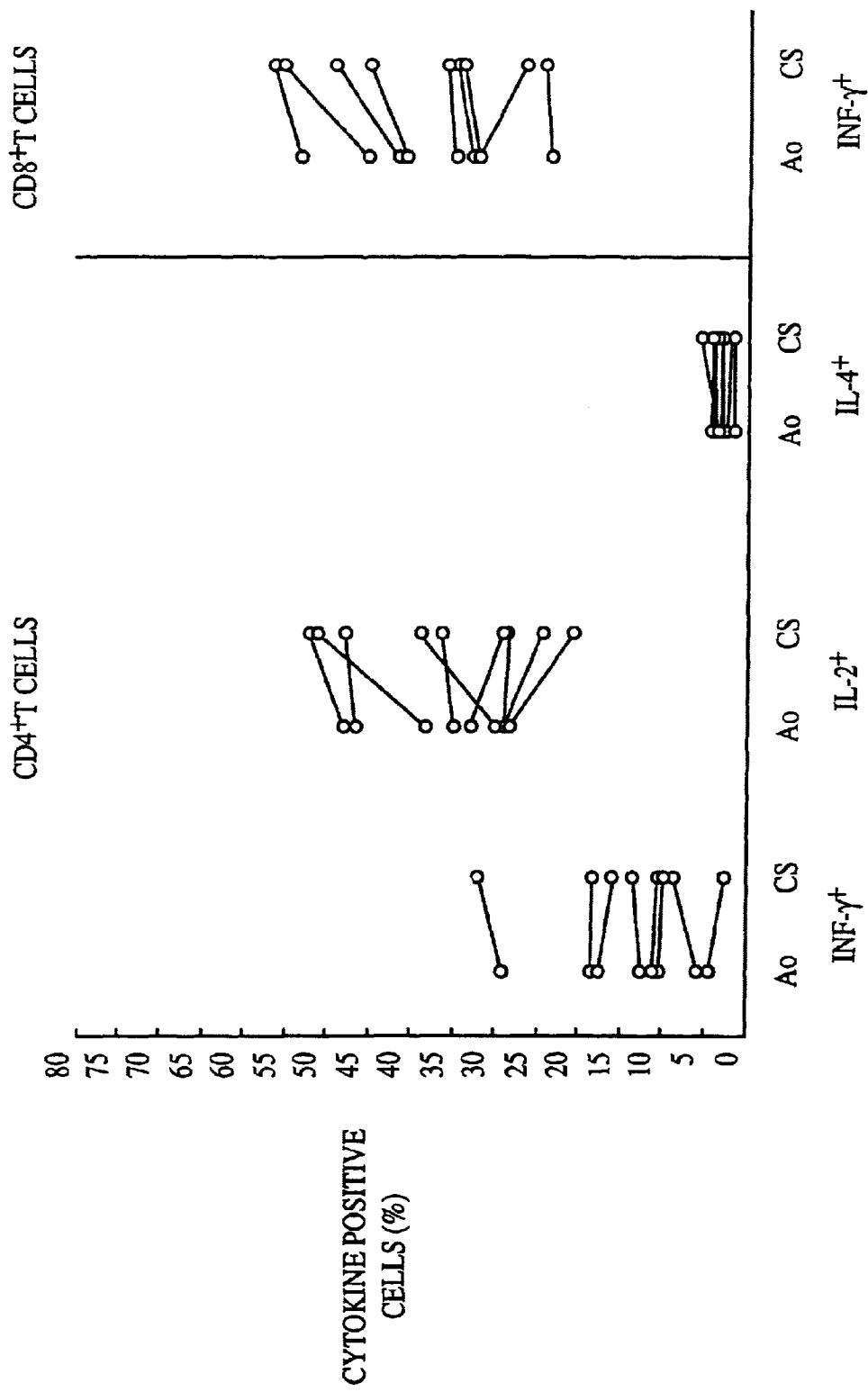
FIG. 3 is two graphs plotting the percent of $CD4^+$ or $CD8^+$ T cells taken from the aortic root (Ao) or the coronary sinus (CS) in nine stable angina patients (panel A) and eight unstable angina patients (panel B) that produce IFN-γ, IL-2, or IL-4.
Figure 3B:
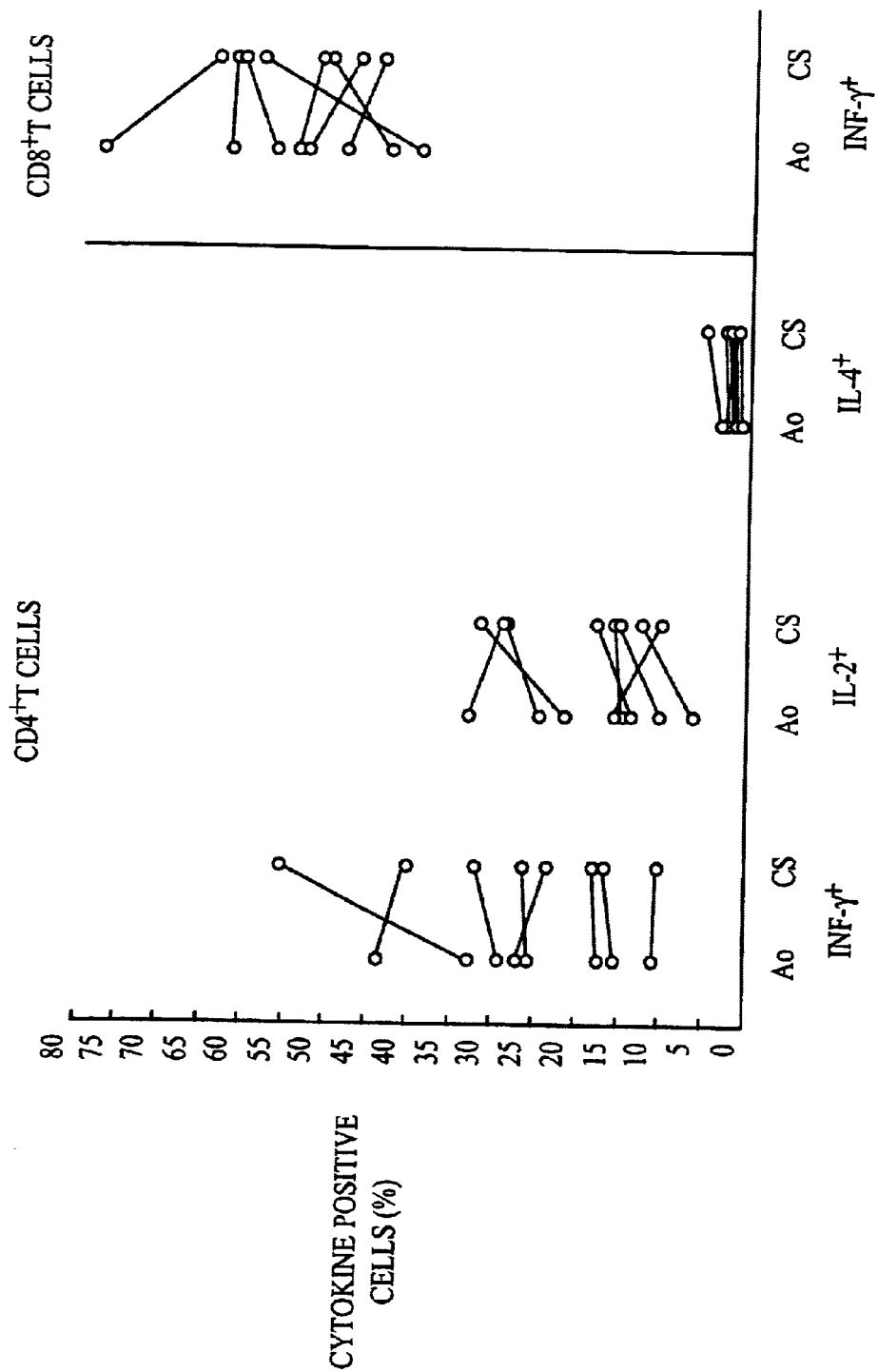

Expansion of IFN-γ Producing CD4$^+$ and CD8$^+$ T Cells is a Stable Feature in Patients With UA Deviations in the functional T cell profile in patients with SA or UA could possibly develop as a consequence of having angina. To approach this, a longitudinal study was used to monitor the patients over a three month period. Blood samples from 18 (86%) UA patients and 15 (60%) SA patients from the original study group were collected 7–14 days after hospital discharge. Blood samples from 76% of the UA patients and 60% of the SA patients were also collected three months following the initial analysis. In UA donors, the frequencies of CD4$^+$IFN-γ$^+$ and CD8$^+$IFN-γ$^+$ cells declined one to two weeks after discharge but returned to their original levels after three months (FIG. 2). At both time points, the patients were free of symptoms. CD4$^+$IL-2$^+$ and CD4$^+$L-4$^+$ cells were characterized by a reciprocal course with an intermittent increase at 7–14 days after discharge and a rebound after three months to initial frequencies (FIG. 2).

Longitudinal monitoring thus revealed three interesting aspects. First, the perturbations in the T cell population with expansion of IFN-γ-producing CD4$^+$ and CD8$^+$ T cells in UA and over representation of CD4$^+$IL-2$^+$ and CD4$^+$IL-4$^+$ T cells in SA were maintained over time and were detectable independent of acute chest pain. Second, homeostatic mechanisms involved in regulating the composition of T cell subsets were suggested by the finding that UA patients had transient variations in the cell frequencies, only to return to initial levels. Third, frequencies of IFN-γ-producing and IL-2-producing T cells appeared to be inversely, instead of directly, correlated.

The possibility that the transient loss in IFN-γ$^+$ T cells combined with a gain in IL-2$^+$ T cells was associated with therapeutic intervention was explored. While in the hospital, patients with UA received heparin, which was discontinued after resolution of acute symptoms. No other therapeutic intervention could be associated with variations in the frequencies of cytokine-producing T cells.

In addition, the influence of interventions such as angioplasty, stent implantation, and coronary artery by-pass surgery on functional T cells was addressed. The patient cohorts were divided into subsets with or without intervention. For UA as well as SA patients, frequencies of IFN-γ-producing and IL-4-producing T cells at all three time points were independent of intervention (data not shown).

Example 3

Expansion of CD4$^+$CD28$^{null}$ T Ccells in Patients With UA

Figure 4:
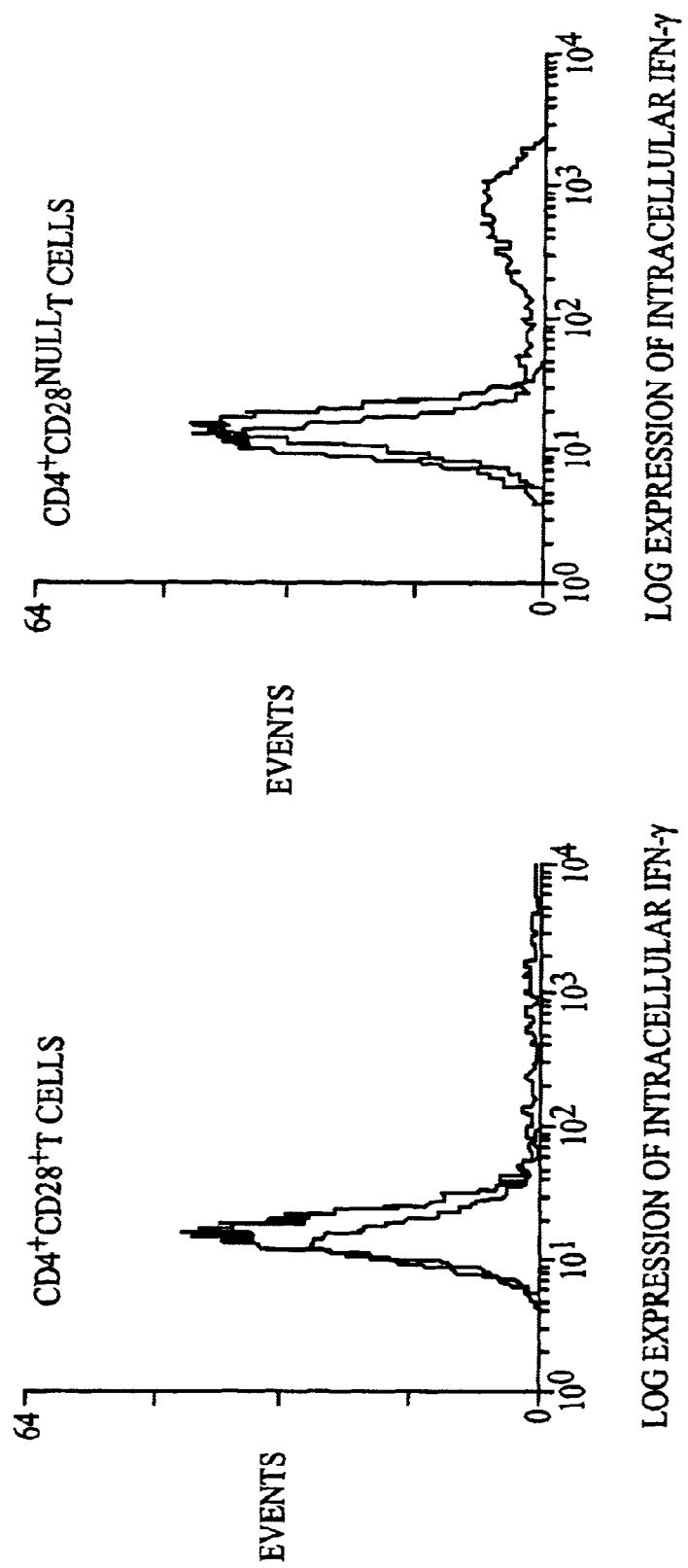
FIG. 4 is two graphs plotting the log expression of intracellular IFN-γ for $CD4^+/CD28^+$ and $CD4^+/CD28^{null}$ T cells from unstable angina patients. The black line (outer trace) corresponds to the expression of IFN-γ and the gray line (inner trace) corresponds to an isotype control.

Three-color flow cytometric analysis of IFN-γ-synthesizing T cells was performed in 16 out of 21 UA patients. Results of a typical experiment are shown in FIG. 4. In the 16 UA patients analyzed, 32.4% of the CD4$^+$CD28$^{null}$ and 15.8% of the CD4$^+$CD28$^+$ T cells had cytoplasmic IFN-γ ($P<0.01$). The mean fluorescence of positive cells was significantly higher in the CD28$^{null}$ than in the CD28$^+$ population (229.3 versus 179.8, $P<0.01$), suggesting increased IFN-γ production at the single-cell level.

Figure 5:
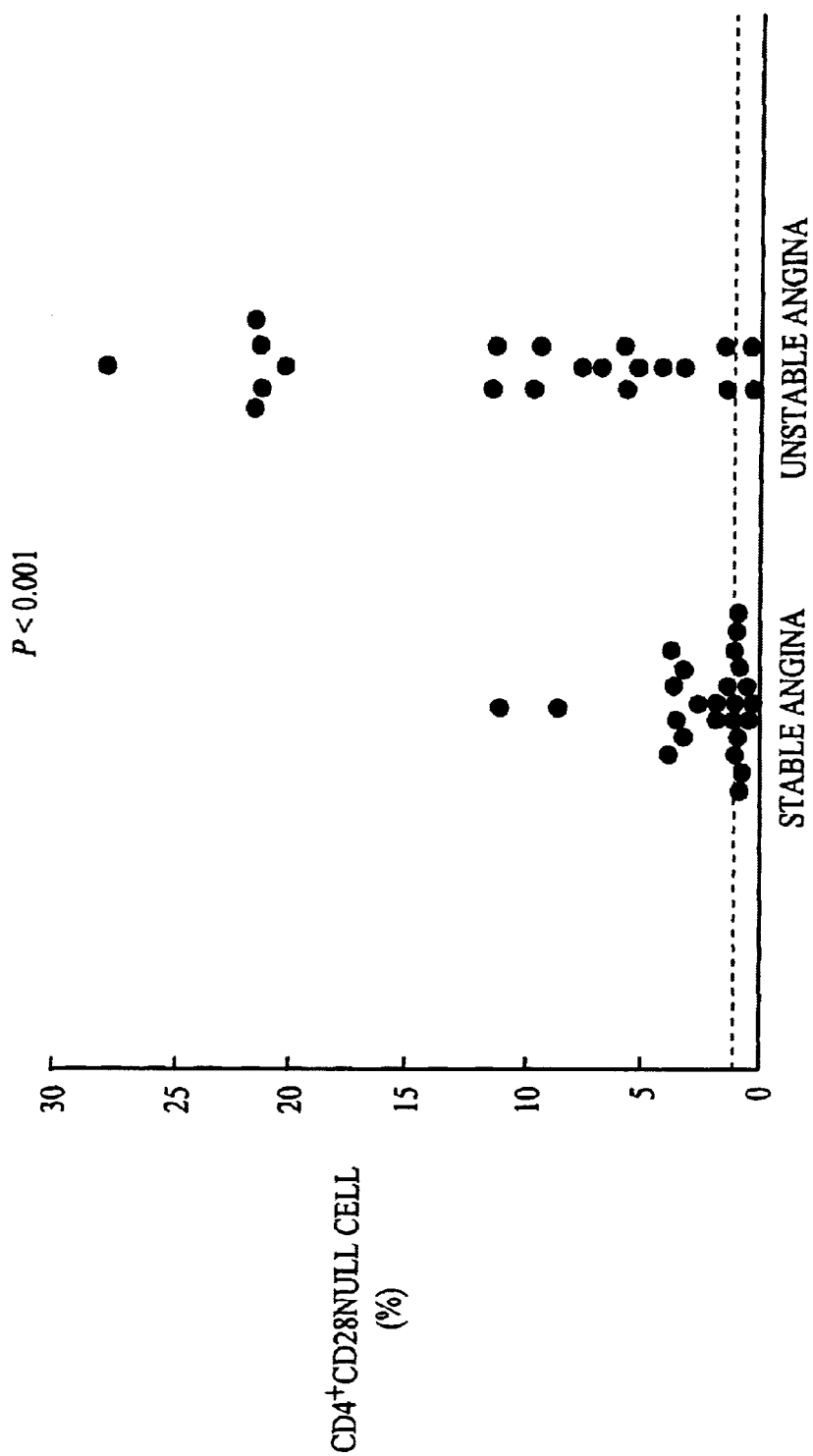
FIG. 5 is a graph depicting the percent of $CD4^+/CD28^{null}$ cells in stable and unstable angina patients. The dashed line represents the 1.1% cutoff that has been determined to distinguish "non-carriers" from "carriers" of $CD4^+/CD28^{null}$ T cells in a population of healthy subjects.

CD4$^+$CD28$^{null}$ T cells are infrequent in normal donors. All 25 patients with SA and all 21 patients with UA were evaluated for the presence of CD4$^+$ T cells lacking CD28 expression. The results are shown in FIG. 5 and demonstrate that the expansion of the CD4$^+$CD28$^{null}$ T cell subset was characteristic of patients with UA. In the patient group with SA, 52% of the individuals had less than 1.1% CD4$^+$CD28$^{null}$ T cells. Only a single individual had more than 10% CD4$^+$CD28$^{null}$ T cells. Conversely, only two patients with the diagnosis of UA had less than 1.1% CD4$^+$CD28$^{null}$ T cells, but 38% of this patient subset had more than 10% CD4$^+$CD28$^{null}$ T cells. Median frequencies of CD4$^+$CD28$^{null}$ T cells were 1.0% for the SA patients and were 8-fold higher (7.8%) in the UA patients ($P=0.001$). These findings demonstrated a marked alteration in the composition of the T cell compartment in individuals with UA.

Figure 6:
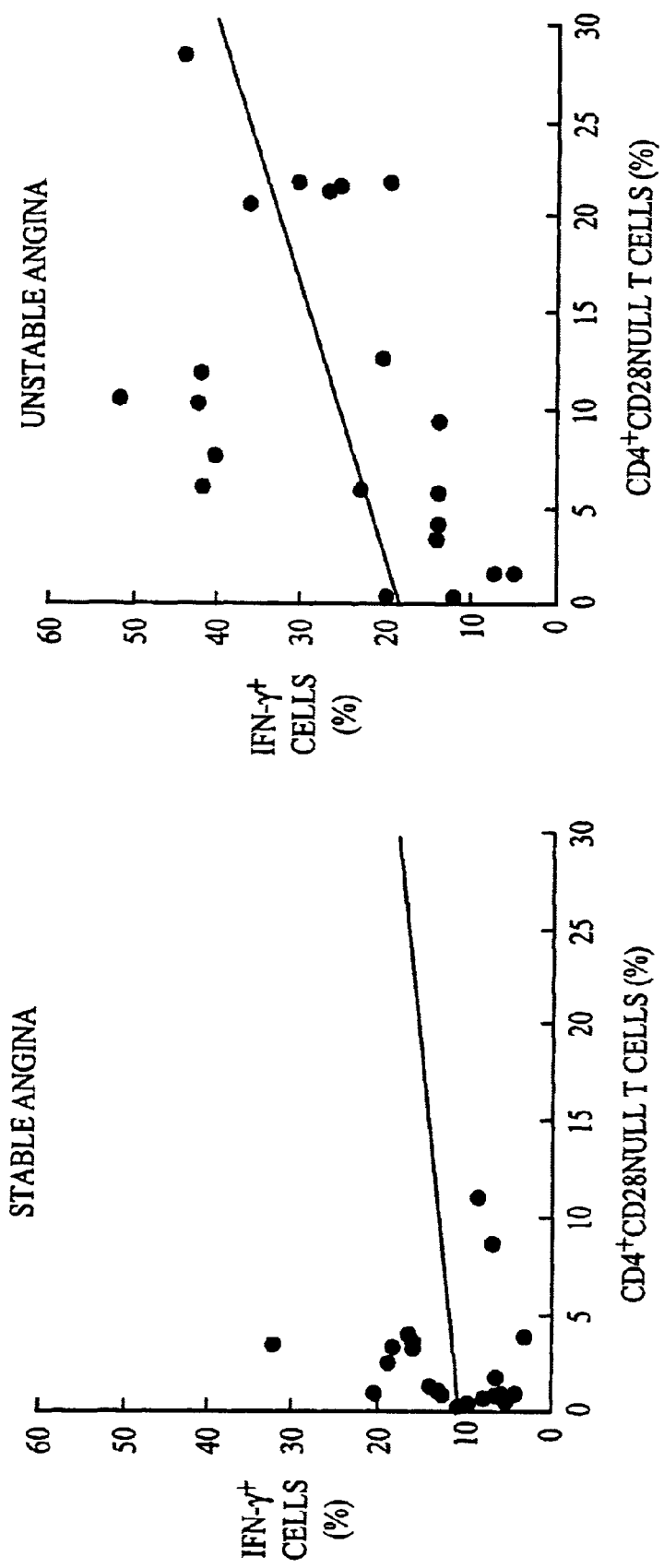
FIG. 6 is two graphs depicting the correlation between IFN-γ production and the increased frequencies of $CD4^+/CD28^{null}$ T cells in unstable angina.

To address the question whether the accumulation of CD4$^+$CD28$^{null}$ T cells in the repertoire of UA patients had functional consequences and biased the repertoire towards IFN-γ production, the frequency of CD4$^+$CD28$^{null}$ T cells was compared with the number of IFN-γ-secreting cells as shown in FIG. 6. This analysis showed a positive correlation (Spearman rank correlation test; R=0.64, P=0.002), suggesting that CD4$^+$CD28$^{null}$ T cells are a major contributing factor in the increased IFN-γ production in UA patients. A significant correlation, however, was not found in the stable angina patients (R=0.30, P=0.12).

The above results indicate that UA patients are characterized by a perturbation of the T cell repertoire with expansion of CD4$^+$ and CD8$^+$ T cells committed to the production of IFN-γ. Not only were IFN-γ$^+$ T cells increased in frequency, more importantly, they also expressed an unusual CD4$^+$CD28$^{null}$ phenotype.

Although the invention is not limited to any mode of action, the following may be involved in coronary heart disease. IFN-γ is the most potent stimulator for monocytes/macrophages. Excessive release of this cytokine will undoubtedly lead to monocyte/macrophage activation with concomitant production of pro-inflammatory mediators, including IL-6. Such an acute phase response in UA patients could be regarded as a downstream effect of an altered composition of the functional T cell repertoire. In this case, UA is a syndrome with abnormalities in the immune response of affected individuals. Understanding the mechanism of this immunodeviation can lead to identification of the ultimate cause of this acute coronary syndrome and can provide molecular targets for therapeutic interventions.

Several lines of evidence support the model that CD4$^+$CD28$^{null}$ T cells arise in response to chronic antigenic stimulation. CD28 is a major costimulatory molecule (Linsley and Ledbetter, *Annu. Rev. Immunol.* 11:191–212 (1993)), and triggering of CD28 by ligands expressed on the surface of antigen presenting cells provides the necessary second signal to complete antigen-mediated T cell stimulation. The fate of a T cell recognizing antigenic peptide is entirely determined by the costimulatory signal. Absence of costimulation induces anergy or death of the T cell (Boise et al., *Immunity* 3:87–98 (1995)). Likewise, chronic recognition of antigen could induce down-regulation of CD28. Loss of CD28 expression in CD4$^+$CD28$^{null}$ T cells is associated with the absence of two nuclear transcription factors that bind to DNA-binding motifs within the minimal promoter of the CD28 gene (Vallejo AN et al., *J. Biol. Chem.* 273:8119–8129 (1998)). Exposure of normal CD4$^+$CD28$^+$ T cells to antigens causes a transient down-regulation of the CD28 gene-specific nuclear transcription factors, raising the possibility that persistence of antigen will eventually result in the loss of CD28. Antigen-derived proliferation of CD4$^+$CD28$^{null}$ T cells would also explain why these cells have a tendency to undergo clonal expansion in vivo (Schmidt D et al., *Molec. Med.* 2:608–618 (1996)).

In addition to continuous antigenic stimulation, genetic factors may contribute to the emergence of CD4$^+$CD28$^{null}$ T cells, as suggested by the high concordance for monozygotic twins, but not for husband/wife pairs, in the expression of CD4$^+$CD28$^{null}$ T cells (data not shown). The emergence of CD4$^+$CD28$^{null}$ cells may, therefore, reflect the existence of a genetic risk factor that predisposes individuals to develop UA.

The current data confirm that T lymphocytes are activated in patients with stable as well as unstable angina, but the precise nature of the activation pattern distinguishes the two types of disease. More importantly, these results provide a correlation between increased frequencies of CD4$^{+CD}$28$^{null}$ T cells, increased IFN-γ secretion, and the occurrence of instability, suggesting that IFN-γ is a critical mediator in UA. It remains to be resolved how exactly CD4$^+$CD28$^{null}$ T cells are stimulated in UA patients and whether effector functions in addition to IFN-γ release play a role in the disease process.

CD4$^+$CD28$^{null}$ T cells cannot be costimulated through the CD28-CD80/CD86 pathway but must use an alternate, presently unidentified, costimulatory system. This raises the question as to which microenvironment provides optimal stimulatory conditions and facilitates the expansion and activation of CD28$^{null}$ T cells. The atherosclerotic plaque could represent such an environment and could, thus, be the source for the expanding cell population in UA. The expression of the costimulatory molecule required to complete the antigen-triggered stimulation of CD4$^+$CD28$^{null}$ T cells will dictate the tissue tropism of such cells. Expression of the ligand for this molecule on endothelial cells would be a mechanism guiding these T cells to the vascular wall.

To understand how CD4$^+$CD28$^{null}$ T cells could contribute to vascular injury, gene expression for a series of molecules involved in T cell effector functions have been explored. CD28-deficient T cells lack transcription of the CD40 ligand (CD40L) gene and, therefore, lack the ability to interact with B cells. Defective expression of CD40L essentially excludes a role of these T cells in antibody-mediated immune responses. Rather, CD4$^+$CD28$^{null}$ T cells transcribed the genes for perforin and granzyme B. Perforin is a pore-forming molecule that creates cylindrical pores in the membrane of target cells. Production of perforin is highly regulated and identifies T cells capable of cytotoxicity. It is therefore possible that CD4$^+$CD28$^{null}$ T cells, in addition to their secretion of IFN-γ and subsequent activation of macrophages, exhibit cytotoxic activity in atherosclerotic lesions and contribute to plaque instability by direct mechanisms.

In summary, patients with unstable angina express an unusual subset of T cells that are committed to the production of IFN-γ. In addition, patients with stable angina have a distinct cytokine pattern characterized by an increased proportion of CD4$^+$ T cells producing IL-2 and IL-4.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for classifying an angina condition in a patient, said method comprising:
 a) determining the frequency of CD4$^+$/CD28$^{null}$ cells in said patient,
 b) comparing said frequency of CD4$^+$/CD28$^{null}$ cells to a reference frequency to obtain information about said angina condition, and
 c) classifying said angina condition as stable or unstable based on said information.

2. The method of claim 1, wherein determining the frequency of CD4$^+$/CD28$^{null}$ cells comprises measuring the percentage of CD4$^+$ cells that are CD4$^+$/CD28$^{null}$ cells.

3. The method of claim 1, wherein said reference frequency is derived from the CD4$^+$/CD28$^{null}$ cell frequencies from a population.

4. The method of claim 3, wherein said population comprises a population of unstable angina patients.

5. The method of claim 3, wherein said population comprises a population of stable angina patients.

6. The method of claim 3, wherein said population comprises a population of healthy individuals.

7. The method of claim 3, wherein said reference frequency is expressed as the percentage of $CD4^+$ cells that are $CD4^+/CD28^{null}$ cells.

8. The method of claim 7, wherein said reference frequency is greater than about 2.0 percent.

9. The method of claim 7, wherein said reference frequency is less than about 2.0 percent.

10. A method for determining the predisposition of an individual to have a stable or unstable angina condition, said method comprising:
   a) determining the frequency of $CD4^+/CD28^{null}$ cells in said individual,
   b) comparing said frequency of $CD4^+/CD28^{null}$ cells to a reference frequency to obtain information about said individual, and
   c) classifying said individual as being predisposed to have a stable or unstable angina condition based on said information.

* * * * *